United States Patent [19]

Siekierka et al.

[11] Patent Number: 5,196,352
[45] Date of Patent: Mar. 23, 1993

[54] NEW FK-506 CYTOSOLIC BINDING PROTEIN

[75] Inventors: John J. Siekierka, Nutley; Hsuen-Yun Hung, East Brunswick; Marie J. Staruch, Toms River; Nolan H. Sigal, Westfield; Richard A. Mumford, Red Bank, all of N.J.

[73] Assignee: Merck & Co., Inc., Rahway, N.J.

[21] Appl. No.: 722,066

[22] Filed: Jun. 27, 1991

Related U.S. Application Data

[60] Division of Ser. No. 548,429, Jul. 5, 1990, Pat. No. 5,109,112, which is a continuation of Ser. No. 369,576, Jun. 21, 1989, abandoned, which is a continuation-in-part of Ser. No. 300,659, Jan. 19, 1989, abandoned.

[51] Int. Cl.$^5$ ............................................. G01N 33/566
[52] U.S. Cl. ........................................ 436/501; 435/7.1; 530/413; 530/417
[58] Field of Search ................ 530/350, 387, 391–397, 530/412, 413, 414, 417; 435/7.1, 7.31; 514/2, 12; 436/501

[56] References Cited

U.S. PATENT DOCUMENTS

4,722,999  2/1988  Handschumacher et al. ...... 530/412
5,109,112  4/1992  Siekierka ............................ 530/350

OTHER PUBLICATIONS

Harding, M. W. et al. Nature 341:758–760, Oct. 26, 1989, "A Receptor for Immunosuppc. FK506 ...".
Siekierka, J. J. et al. Nature 341: 755–757–Oct. 26, 1989, "A cytosolic Binding Protein ...".
Siekierka, J. J. et al. J. Immnol. 143: 1580–83, Sep. 1, 1989, "FK506, 9 Potent Novel Imur ...".
Bih-Hwa shieh, et al., *The ninA gene required for visual transduction in Drosophia encodes a homologue of cyclosporin A-binding protein*, Nature, vol. 338, pp. 67–70 (Mar. 2, 1989).
Schneuwly, et al., *Drosophila ninaA gene encodes an eye-specific cyclophilin (cyclosporin A binding protein*, Proc. Natl. Acad. Sci. U.S.A. vol. 86, pp. 5390–5394, Jul. 1989, Cell Biology.
Handschumacher, et al., *Cyclophilin: A Specific Cystosporin Binding Protein for Cyclosporin A*. Science, vol. 226, pp. 544–547 (Nov. 1984).
*Tumor Immunology Bank*, ATCC Update–Cell Lines & Hybridomas–May 1990 Supplement.
Haendler, et al., *Complementary DNA for Human T-cell Cyclophilin*, EMBO Journal, vol. 6, No. 4, pp. 947–950 (1987).
Kronke, et al., *Cyclosporin a inhibits T-cell growth factor gene expression at the level of mRNA transcription*, Proc: Natl. Acad. Sci. USA, vol. 81, pp. 5214–5218, Aug. 1984 Immunology.
Elliot, et al., *Induction of Interleukin 2 Messenger RNA Inhibited by Cyclosporin A*, Science, 226, pp. 1439–1441 (1984).

(List continued on next page.)

*Primary Examiner*—Christine M. Nucker
*Assistant Examiner*—T. Cunningham
*Attorney, Agent, or Firm*—Robert J. North; Charles M. Caruso

[57] ABSTRACT

A new homogeneous cytosolic binding (HCB) protein, having a specific binding activity of about 26 μg FK-506 per mg protein and a molecular weight of about 10-12 kilodaltons, reversibly binds the immunosuppressant FK-506 but not cyclosporine A (CSA). The protein is stable to heating at 56 degrees C. for 30 minutes retaining its FK-506 binding affinity, and has the (partial) amino terminal amino acid sequence: $H_2N$ G y V l G n V l G u T r I e S r P o G y A p G y A g T r P e P o L s A g-Gly-Gln-Thr-X-Val-Val-Val-His-Tyr-Thr-Gly-Met-Leu-Glu-Asp-Fly-Lys-Phe-ASp (wherein X is undefined). The HCBV protein is isolated from the cytosol of mammalian tissues, preferably human neoplastic T-cell lines, e.g. Jurkat, and can be used in diagnostic and purification procedures involving FK-506 macrolide type immunosuppressants. The HCB protein also catalyses the cis-trans isomerization of proline-containing peptide bonds.

8 Claims, 6 Drawing Sheets

OTHER PUBLICATIONS

Goldsmith, et al., *Isolation and characterization of a T-lymphocyte somatic mutant with altered signal transduction by the antigen receptor*, Proc. Natl. Acad. Sci. uSA, vol. 84, pp. 6879–6883, Immunology (Oct. 1987).

Stern, et al., *Purification to homogeneity and partial characterization of interleukin 2 from a human T-cell leukemia*, Proc. Natl. Acad. Sci. USA vol. 81, pp. 871–875, Immunology (Feb. 1984).

Stewart, et al., *Perturbation of the human T-cell antigen receptor-T3 complex leads to the production of inositol tetrakisphosphate: Evidence for conversion from inositol trisphosphate*, Proc. Natl. Acad. Sci. USA, vol. 83, pp. 6098–6102, Immunology (Aug. 1986).

Gillis, et al., *Biochemical and Biological Characterization of Lymphocyte Regulatory Molecules: V. Identification of an Interleuken 2-producing Human Leukemia T Cell Line*, J. Exp. Med., vol. 152, pp. 1709–1719 (1980).

Siekierka, et al., *The Cytosolic-binding Protein for the Immunosuppressant FK-506 is Both a Ubiquitous and Highly Conserved Peptidyl-Prolyl Cis-Trans Isomerase*, J. of Biol. Chem., vol. 265, No. 34, pp. 21011–21015 (1990).

Merker, et al., *Uptake and Nature of the Intracellular Binding of Cyclosporin A in a Murine Thymoma Cell Line, BW5147[1]*, J. of Immun vol. 132, No. 6, (Jun. 1984).

Harding, et al., *Isolation and Amino Acid Sequence of Cyclophilin*, J. of Biological Chem., vol. 261, No. 18, pp. 8547–8553 (1986).

Warty, et al., *FK506: A Novel Immunosuppressive Agent/Characteristics of Binding and Uptake by Human Lymphocytes*, Transplantation, vol. 46, pp. 453–455 (1988).

Sawada, et al., *Novel Immunosuppressive Agent. FK506/In Vitro Effects on the cloned T Cell Activation*, J. of Immunology, vol. 139, pp. 1797–1803, No. 6 (1987).

Siekierka, et al., *FK506, a potent novel immunosuppressive agent, binds to a cytosolic protein which is distinct from the cyclosporin A-binding protein, cyclophilin*, J. of Immun., vol. 143, pp. 1580–1583, No. 5, (1989).

NEW FK-506 CYTOSOLIC BINDING PROTEIN

CROSS REFERENCE TO RELATED APPLICATIONS

The instant case is a divisional case of U.S. Ser. No. 548,429, filed Jul. 5, 1990, now U.S. Pat. No. 5,109,112, which in turn is a continuation case of U.S. Ser. No. 07/369,576, filed Jun. 21, 1989, now abandoned, which in turn is a continuation-in-part case of U.S. Ser. No. 07/300,659, filed Jan. 19, 1989, now abandoned.

BACKGROUND OF THE INVENTION

1. Field of the Invention

The present invention relates to a new homogeneous cytosolic binding (HCB) protein which binds FK-506 but not cyclosporine A, is stable to heating at 56° C. for 30 minutes, and has a molecular weight of about 10-12 kilodaltons The (partial) amino terminal amino acid sequence of the HCB protein is: $H_2N$-Gly-Val-Gln-Val-Glu-Thr-Ile-Ser-Pro-Gly -Asp-Gly-Arg-Thr-Phe-Pro-Lys-Arg-Gly-Gln-Thr-X-Val-Val-His-Tyr-Thr-Gly-Met-Leu-Glu-AsP-Gly-Lys-Lys-Phe-Asp (wherein X is undefined). The HCB protein has peptidyl-proline isomerase enzymatic activity.

2. Brief Description of Disclosures in the Art

In 1983, the US FDA licensed cyclosporine, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more potent than cyclosporine. The macrolide is produced by fermentation of a particular strain of *Streptomyces tsukubaensis*. Also described is the closely related macrolide immunosuppressant FK-520, produced by *S. hygroscopicus* subsp. *yakushimaensis*.

FK-506 shares a number of immunosuppressive properties with the cyclic peptide, cyclosporine A, though 10-100 times more potent in this regard. These similarities suggest that both agents may share a similar mechanism of action at the biochemical level.

For example, Cyclosporine A is known to bind with the cytosolic protein, cyclophilin, as described in SCIENCE, Vol. 226, pp. 544-546 (Nov. 1984) by R. E. Handschumacher et al, which is thought to mediate the immunosuppressive effects of cyclosporine A in cells. Cyclophilin has also been shown to possess an enzymatic activity, which catalyzes the cis-trans isomerization of peptidyl prolyl bonds, as described in *Nature*, Vol. 337, pp 473-475 and pp. 476-478 by N. Takahashi et al. and Fischer et al., respectively.

Further, the article by V. Warty et al in *Transplantation* Vol. 46, No. 3, pp. 453-455 (September 1988) present data suggesting that FK-506 also binds a cytosolic protein with an apparent molecular weight of about 18-19 kilodaltons which is similar to the protein that also binds cyclosporine.

What is needed in the art is the isolation and identification of that particular FK-506 binding protein in order to help delineate the FK-506 mechanism of therapeutic action in the cell.

SUMMARY OF THE INVENTION

We have identified a homogeneous cytoplasmic binding (HCB) protein for FK-506 in the neoplastic human T-cell line, JURKAT, using [$^3$H]FK-506. It is believed that this protein is ubiquitous and is present in a variety of normal human cells and tissues and particularly is abundant in neoplastic and transformed human T-cell lines, preferably the JURKAT cell line, which is readily available at the American Type Culture Collection, 12301 Parklawn Drive in Rockville, Md., under the designation "JURKAT TIB-152, Clone E6-1 Human Acute T-cell Leukemia, deposited by Arthur Weiss.

The HCB protein has a molecular weight of 10-12 kilodaltons (as determined by gel filtration), is stable to heating at 56° C. for 30 minutes and does not bind cyclosporine A (CsA). This newly discovered protein contrasts with the CsA binding protein, cyclophilin, described in the above-listed prior art, in which cyclophilin is described as being heat labile and having a molecular weight of 15-17 Kd.

In accordance with this invention there is provided a homogeneous cytosolic binding (HCB) protein having a specific binding affinity for FK-506.

Further characteristics of this HCB protein are that it has no specific binding affinity for cyclosporine A; has a molecular weight in the range of 10-12 kilodaltons; a specific binding activity of about 26 micrograms FK-506 per mg HCB protein; is stable at 56° C. for 30 minutes; is derived from a variety of sources including, for example, normal and neoplastic human T-cell lines; and in particular, the JURKAT cell line, and has the amino terminal amino acid sequence (partially sequenced): NH2-Gly-Val-Gln-Val-Glu-Thr-Ile-Ser-Pro-Gly-Asp-Gly-Arg-Thr-Phe-Pro-Lys-Arg-Gly-Gln-Thr-X-Val-Val-His-Tyr-Thr-Gly-Met-Leu-Glu-Asp-Gly-Lys-Lys-Phe-Asp (wherein X is at yet undefined); and has an enzymatic activity, which catalyzes the cis-trans isomerization of proline-containing peptide bonds.

Also provided is the purified complex formed between a biologically useful ligand and the above-described HCB protein, wherein said ligand possesses a specific binding affinity for the HCB protein. The ligand can be an immunosuppressant, e.g., FK-506 type macrolide, or an antibody to the HCB protein.

Further provided is a method of determining the presence or quantity of a biologically useful ligand, e.g. FK-506, having an affinity for the above-described HCB protein, in a sample, e.g. a body fluid of an immunosuppressed individual on FK-506 therapy, which comprises contacting said sample with the HCB protein, wherein said HCB protein preferably can be immobilized, for example, on a cyanogen bromide activated Sepharose type affinity column.

Furthermore is provided an embodiment of the method to purify a biologically useful ligand wherein said ligand is present in a sample comprising a fermentation broth, a biological fluid, e.g. human blood, or is a chemical entity that is a potential drug, and wherein said ligand is preferably an immunosuppressant, e.g. FK-506, or is an antibody to the HCB protein.

Figure 2:
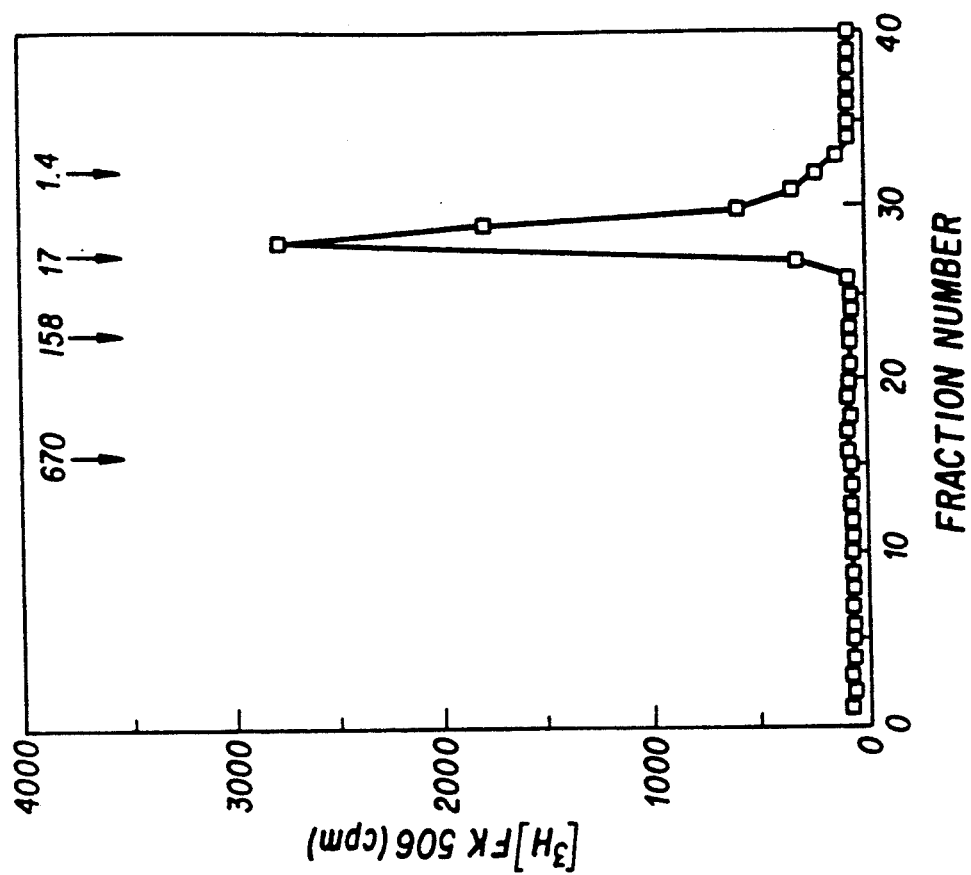
FIG. 2 illustrates the fractionation of cytoplasmically associated [³H] FK-506 by HPLC gel filtration.
Figure 1:
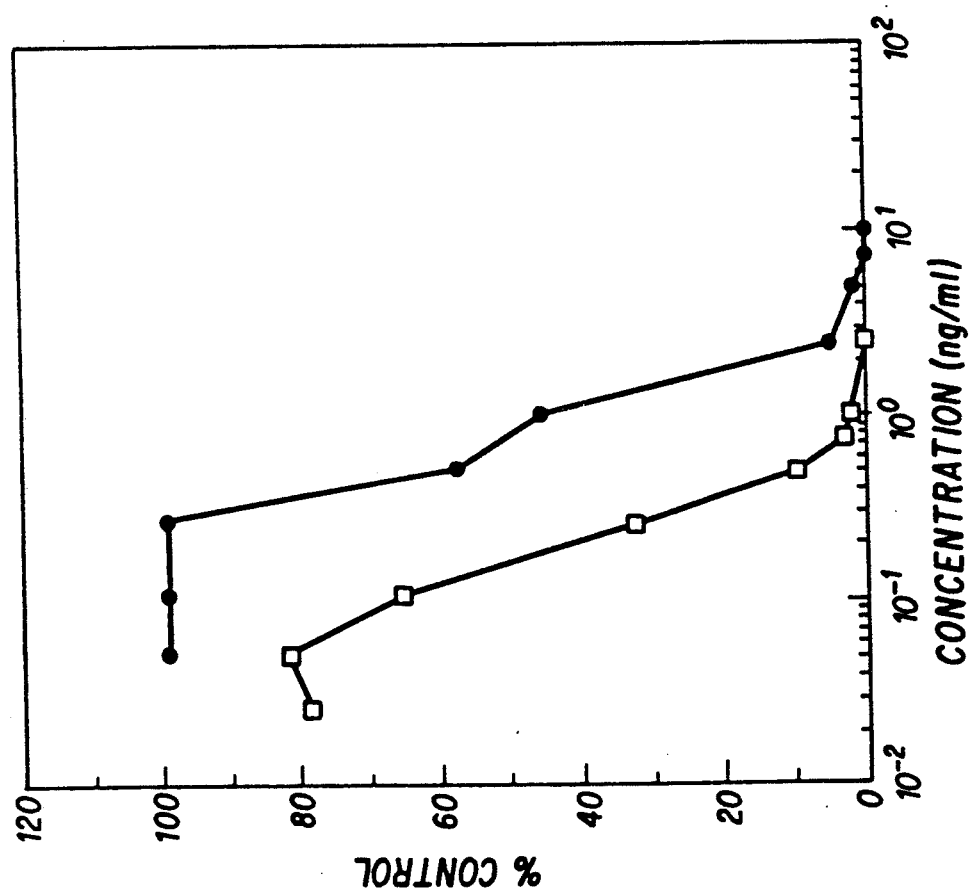
FIG. 1 illustrates inhibition of IL-2 secretion in JURKAT cells stimulated with PMA and ionomycin by FK-506 and [$^3$H]-dihydro FK-506.

The specification contains a more detailed description of FIGS. 1-8 in the section headed "Figure Legends".

DESCRIPTION OF THE INVENTION AND PREFERRED EMBODIMENTS

We have demonstrated the presence of a heat stable, low molecular weight cytosolic binding protein for the potent immunosuppressive agent FK-506, in JURKAT cells. The HCB protein appears to be distinct from cyclophilin by a number of criteria including, molecular weight, heat stability, ligand specificity and amino acid sequence. This does not, however, rule out the possibility that the two binding proteins are related, perhaps as members of the recently identified cyclophilin family (B. Haendler et al., EMBO J. 6, 947 (1987)). These low molecular weight proteins may constitute part of a signal transduction pathway utilized during T-cell activation which is important for activation of select lymphokine genes (e.g. IL-2).

The potent immunosuppressive agent, cyclosporine A (CsA), has found wide clinical use in the prevention of allograft rejection and treatment of graft versus host disease (B. D. Kahan, Cyclosporin: Biological Activity and Clinical Applications (Grune & Stratton, Orlando, Fla., 1983). CsA appears to act specifically during T lymphocyte activation by inhibiting the transcription of a limited set of early T-cell activation genes (IL-2, IL-3, gamma-IFN, GM-CSF, TNF and c-myc) (J. F. Elliot et al., Science 226, 1439 (1984); M. Kronke et al., Proc. Natl. Acad. Sci. USA 81, 5214 (1984). A recently isolated macrolide, FK-506, obtained from Streptomyces tsukubaensis has been shown to possess very similar, if not identical, immunosuppressive properties both in vivo and in vitro, though being 10-100 times more potent than CsA in this regard (S. Sawada et al., J. Immunol. 139, 1797 (1987)). Studies on the biochemical nature of the immunosuppressive pathway affected by CsA have led to the purification and characterization of a specific CsA binding protein termed, cyclophilin (R. E. Handschumacher et al., Science 226, 544 (1984); M. W. Harding et al., J. Biol. Chem. 261, 8547 (1986)). Two isoforms of cyclophilin have been isolated which bind CsA with identical affinities and exhibit a structure-function profile consistent with playing a role in immuno-suppression. Recently, it has been reported that FK-506 may bind to and function via a cytoplasmic receptor (V. Warty et al., Transplantation, 46, p. 453 (1988)).

FK-506 was isolated from a culture of Streptomyces tsukubaensis No. 9993. [³H]-dihydro CsA was made by catalytic reduction of the MeBmt double bond in CsA with tritium gas in dimethylformamide solvent using 10% Pd/C catalyst at room temperature, 1 atmosphere pressure, in a shaker apparatus for an hour, followed by purification by reverse phase high pressure liquid chromatography on a Whatman Partisil OD3 column. The specific activity of the obtained [³H]-dihydro CsA was 44 mCi/mg. [³H]-dihydro FK-506 was prepared by catalytic reduction of the allyl double bound in FK-506 by contacting FK-506 in ethyl acetate solvent with tritium gas under 1 atmosphere pressure and room temperature in the presence of 10% Pd/C catalyst for 20 minutes followed by isolating and purifying the material by reverse phase high pressure liquid chromatography to yield the product which had a specific activity of 49 mCi/mg. Dihydro-[³H]FK-506 was a potent inhibitor of IL-2 secretion in JURKAT cells stimulated with phorbol 12-myristate 13-acetate (PMA) and ionomycin (See FIG. 1 and the following description under "Figure Legends"), although 5 times less potent than the parent compound.

In order to examine the subcellular distribution of [³H]FK-506 binding, JURKAT cells were incubated with [³H]FK-506 for 30 min., washed, lysed in hypotonic buffer and fractionated into cytosol, nuclei and membrane fractions. Greater than 95% of the [³H]FK-506 is specifically associated with the cytoplasmic compartment and the remainder distributed about equally between nuclei and plasma membranes (See following Table 1). This is similar to the reported subcellular distribution of CsA which is largely concentrated in the cytosol where it is found associated with a specific binding protein, cyclophilin (M. M. Merker et al., J. Immunol. 132, 3064 (1984)). In view of this, we prepared cytosol from JURKAT cells incubated with [³H]FK-506 and subjected it to size fractionation by HPLC gel filtration (See FIG. 3 and the following description under "Figure Legends").

Figure 3:
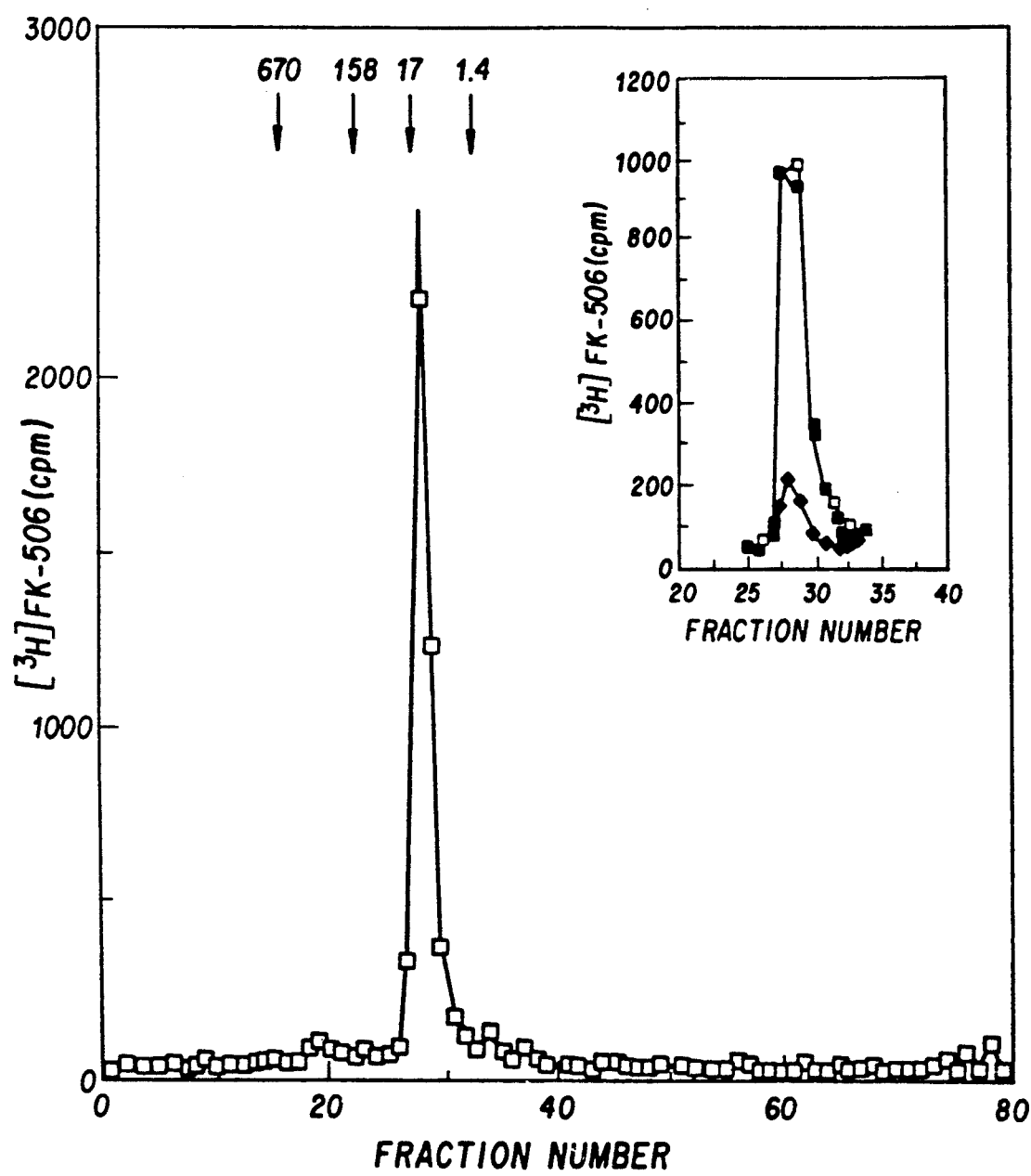
FIG. 3 illustrates direct binding of [³H] FK-506 to a low molecular weight component.
Figure 5:
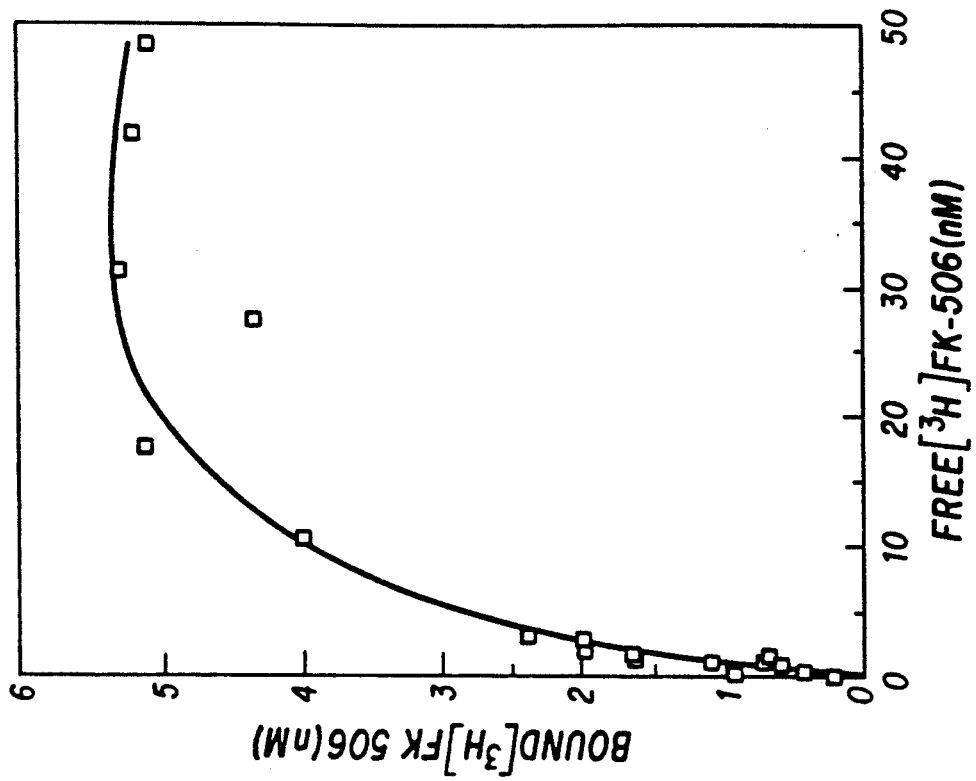
FIG. 5 illustrates binding of [³H] FK-506 to JURKAT cytosol as a function of [³H] FK-506 concentration.
Figure 4:
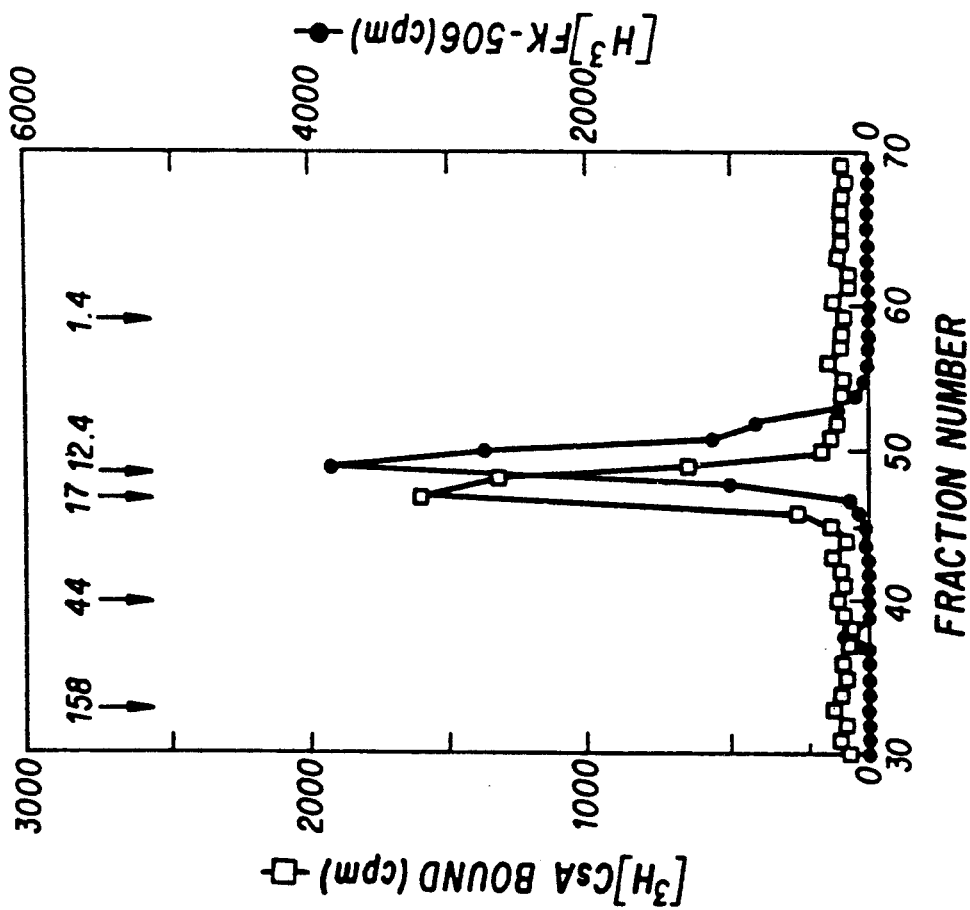
FIG. 4 illustrates the separation of JURKAT cyclophilin from [³H] FK-506 binding activity by HPLC gel filtration.

A single peak of radioactivity was observed eluting at a position corresponding to a molecular weight of 10-12 Kd (FIG. 3). The formation of this complex does not require the intact cell since incubation of JURKAT cytosol with [³H]FK-506 and subsequent HPLC gel filtration yields the same complex (See FIG. 4 and the following description under "Figure Legends"). Inclusion of a 200 fold molar excess of unlabeled FK-506 in the reaction mixture inhibits the formation of this complex by 90% while CsA is without effect (FIG. 4 inset), suggesting that FK-506 binds to a protein other than cyclophilin.

To rule out the possibility that distinct binding sites for both CsA and FK-506 are present on cyclophilin, we assayed highly purified cyclophilin for [³H]CsA and [³H]FK-506 binding using the LH-20 assay developed for cyclophilin (R. E. Handschumacher et al., Science 226, 544 (1984). We could not detect specific binding of [³H]FK-506 to purified calf thymus cyclophilin (See following Table 2). Further characterization of the cytoplasmic component (s) responsible for binding reveals that [³H]FK-506 binding is heat stable (Table 2), while binding of [³H]CsA to crude JURKAT cyclophilin is completely aborgated under these conditions. In order to further delineate CsA and FK-506 binding, we fractionated JURKAT cytosol utilizing HPLC gel filtration and assayed individual fractions for both [³H]CsA and [³H]FK-506 binding using the LH-20 assay. Under our conditions, the peak of [³H]CsA binding elutes at a position corresponding to a molecular weight of 15-17,000, well ahead of the peak of [³H]FK-506 binding (See FIG. 5 and the following description under "Figure Legends") again indicating that both activities are distinct.

Incubation of fractions containing [³H]FK-506 binding activity with proteinase K (Boehringer Mannheim) completely abolished the binding reaction, suggesting that FK-506 forms a complex with a protein.

Figure 6:
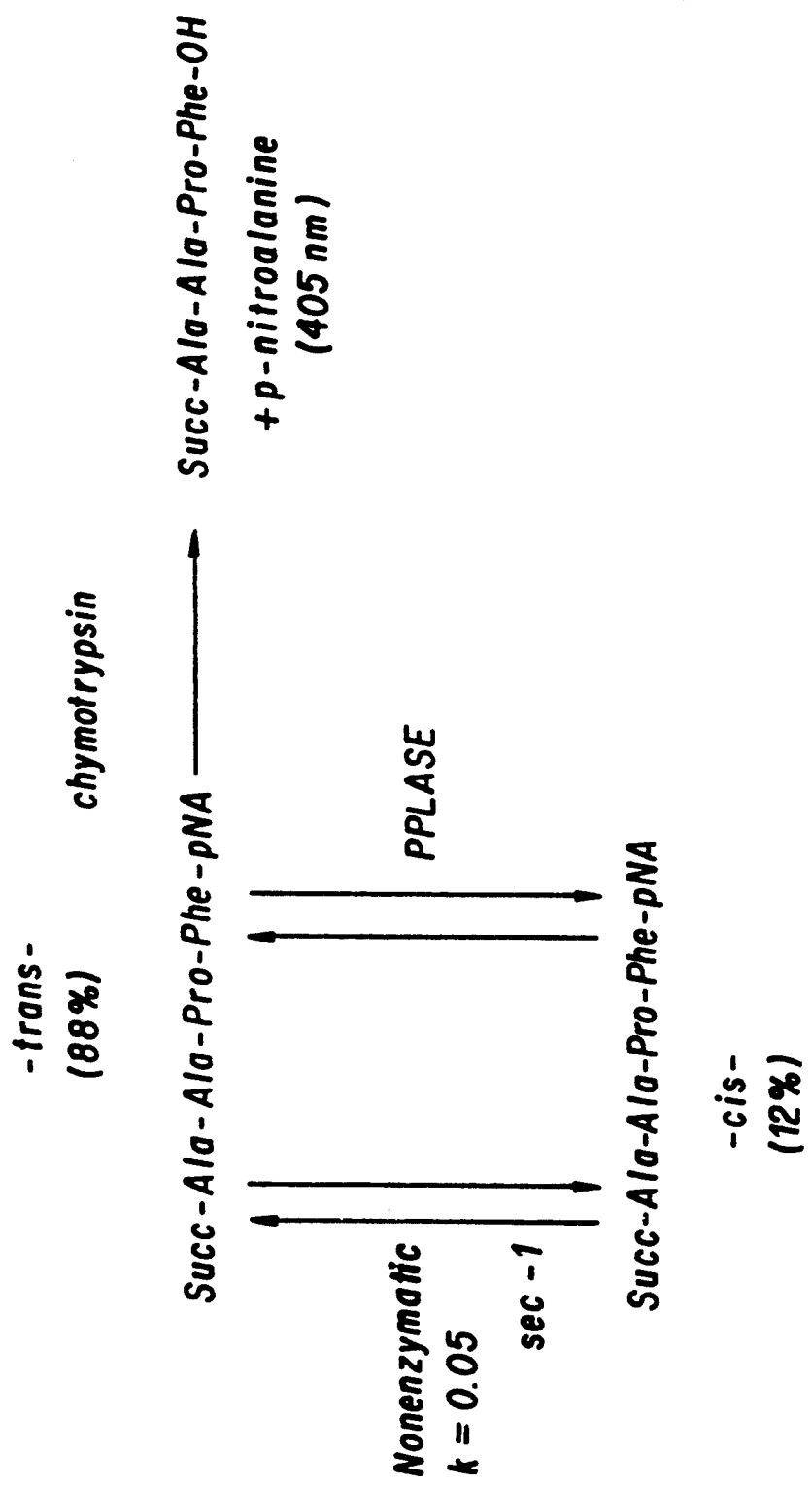
FIG. 6 illustrates the nature of the peptidyl-proline isomerase (PPIase) assay.

Binding of [³H]FK-506 to crude cytosol is saturatable with half maximal binding observed at 4.0 nM (See FIG. 6 and the following description under "Figure Legends"). This value is similar to the concentration of [³H]FK-506 inhibiting IL-2 secretion in JURKAT (1.1 nM) suggesting that the binding observed is physiologically relevant.

FIGURE LEGENDS

FIG. 1.

Inhibition of IL-2 secretion in JURKAT cells stimulated with PMA and ionomycin by FK-506 and [³H]dihydro FK-506. JURKAT cells (equivalent to those available from the ATCC, supra) were cultured in RPMI 1640 media (Cellgro, Mediatech, Wash. D.C.) containing 1% Pen/Strep (Gibco), 1 mM Glutamine and 10% heat-inactivated fetal calf serum (Hazleton). For assay of IL-2 secretion by JURKAT cells, cells were cultured for 16 hr. in 96-well microtiter plates (Costar) at $1 \times 10$ cells/ml in the above media containing 10 ng/ml of PMA (Sigma) and 5 µM ionomycin (Calbiochem) along with the concentrations of FK-506 or [³H]FK-506 indicated. Supernatants (50–100 µl) was assayed for IL-2 using a commercially available ELIZA assay (Collaborative Research Inc.). -▭-▭-▭-, FK-506; -●-●-●-, [³H]-dihydro FK-506.

FIG. 2.

Fractionation of cytoplasmically associated [³H]FK-506 by HPLC gel filtration. Jurkat cells were incubated with 6.2 nM [³H]FK-506 for 30 min. at 37° C. Cells were pelleted as before and resuspended in 250 µl of 10 mM Tris-HCl, pH 7.5 containing 1 mM MgCl₂. After 10 min at 4° C., the cells were lysed by rapidly forcing through a 25 g needle (See M. M. Merker et al., J. Immunol. 132, 3064 (1984). The lysate was centrifuged at $100,000 \times g$ in a Beckman TL-100 ultracentrifuge and 100 µl of supernatant was subjected to HPLC gel filtration on a Bio-Sil TSK-250 column (7.5×300 mm, Bio-Rad Laboratories) at a flow rate of 1 ml/min. Fractions 0.4 ml) were collected and 100 µl of each counted in 10 ml of Aquasol-2. The arrows indicate the elution position of various molecular weight standards (numbers are molecular weight $\times 10^2$) fractionated under identical conditions.

FIG. 3.

Direct binding of [³H]FK-506 to a low molecular weight cytosolic component. A cell-free extract was prepared from JURKAT cells by lysing 40×10 cells in 0.5 ml of 10 mM Tris-HCl, pH 7.5 containing 1 mM MgCl as described in the legend for FIG. 3. 200 µg of protein (Bradford assay, BSA standard, (see M. M. Bradford, *Anal. Biochem.* 72, 248 (1976) was incubated with 16 nM [³H]FK-506 for 10 min at 37° C. 50 µl of the reaction mixture were fractionated by HPLC gel filtration as described in the legend for FIG. 2. The figure inset shows the results of a similar fractionation of the following: -▭-▭-▭-, 200 µg of cytosol and 16 nM [³H]FK-506 alone; -●-●-●-, cytosol, [³H]FK-506 and a 200 fold molar excess of FK-506 and -■-■-■-, cytosol, [³H]FK-506 and a 200-fold molar excess of CsA.

FIG. 4.

Separation of JURKAT cyclophilin from [³H]FK-506 binding activity by HPLC gel filtration 1 0 mg of JURKAT cytosol, prepared as previously described, was subjected to HPLC gel filtration. In order to maximize the separation of low molecular weight components, a Bio-Sil TSK-125 column (7.5×600 mm) was used. 0.4 ml fractions were collected at a flow rate of 1.0 ml/min. 100 µl of each fraction was incubated with 0.5 nM [³H]CsA or [³H]FK-506 and assayed for binding to cytosol components as previously described (6). -▭-▭-▭-, [³H]CsA binding; -♦-♦-♦-, [³H]FK-506 binding.

FIG. 5.

Binding of [³H]FK-506 to JURKAT cytosol as a function of [³H]FK-506 concentration. Binding of [³H]FK-506 was assayed by the LH-20 assay described in Table 2 with 4.9 µg of JURKAT cytosol and the concentrations of [³H]FK-506 indicated. Nonspecific binding, assessed by the amount of [³H]FK-506 bound in the presence of 200-fold molar excess of unlabeled FK-506, has been subtracted but never exceeded 5% of the total cpm bound.

FIG. 6.

Depicted is a summary of the PPIase assay used to measure the cis-trans isomerization of the proline-alanine peptide bond in the peptide, N-succinyl-Ala-Ala-Pro-Phe-p-nitroanilide.

FIG. 7.

Illustrated is HCB protein PPIase activity as a function of HCB protein concentration (A). Symbols (■ ●) represent the results of experiments with 2 different preparations of HCB protein. (B) Comparison of cyclophilin PPIase activity (▭○) and HCB protein PPIase activity (■ ●).

Illustrated is the inhibition of HCB protein PPIase activity of dihydro FK-506; -■-■-■-, CsA; ♦, (A). (B) Illustrates the inhibition of cyclophilin PPIase activity by CSC; -■-■-■-, FK-506; -●-.

TABLE 1

| Subcellular distribution of [³H]FK-506 in JURKAT cells | | |
|---|---|---|
| Fraction (1) | [³H]FK-506 Bound (cpm) | % of Total (2) |
| nuclear pellet | 3,581 | 1.7 |
| plasma membrane | 1,824 | 0.9 |
| cytosol | 207,879 | 97.4 |

(1) $10 \times 10^6$ JURKAT cells were incubated with 6 nM [³H]FK-506 and lysed as described in the legend to FIG. 2. The crude lysate was centrifuged at 2,000 × g for 10 min. to pellet nuclei. The supernatant was centrifuged at 150,000 × g for 20 min. in a Beckman TL-100 ultracentrifuge to pellet crude membranes. Each cell fraction was solubilized in 1% Triton X-100 and counted in 10 ml of Aquasol-2.
(2) The total cpm recovered from all subcellular fractions represents 83% of the total cpm associated with intact cells.

TABLE 2

| Lack of [³H]FK-506 binding to purified cyclophilin and effects of heating on [³H]FK-506 and [³H]CsA binding to JURKAT cytosol | | |
|---|---|---|
| | [³H]FK-506 Bound (cpm)* | [³H]CsA Bound (cpm)* |
| cyclophilin, 100 ng (1) | 0 | 20,988 |
| JURKAT cytosol, 40 µg (2) | 13,585 | 5,988 |
| JURKAT cytosol 40 µg 56 C., | 15,315 | 0 |

TABLE 2-continued

Lack of [³H]FK-506 binding to purified
cyclophilin and effects of heating on [³H]FK-506
and [³H]CsA binding to JURKAT cytosol

| | [³H]FK-506 Bound (cpm)* | [³H]CsA Bound (cpm)* |
|---|---|---|
| 15 min. (2) | | |

*Binding of [³H]FK-506 and [³H]CsA to either purified cyclophilin or JURKAT cytosol was assayed by the LH-20 assay previously described (see R.E. Handschumaker et al., supra). Assays (100 μl) contained 10 mM sodium phosphate, pH 7.4, 5 mM mercaptoethanol and 6.0 nM of either [ H]FK-506 (specific activity = 49 mCi/mg) or [³H]CsA (specific activity = 44 mCi/mg) along with purified cyclophilin or 0.5 nM of either compound with crude JURKAT cytosol. Binding is reported as cpm specifically bound (total cpm bound - cpm bound in the presence of a 200 fold molar excess of unlabeled compound).

AMINO ACID SEQUENCE AND PROTEIN CHARACTERISTICS

The partially determined amino terminal amino acid sequence of the HCB protein is: H₂N-Gly-Val-Gln-Val-Glu-Thr-Ile-Ser-Pro-Gly-Asp-Gly -Arg-Thr-Phe-Pro-Lys-Arg-Gly-Gln-Thr-X-Val-Val-His-Tyr -Thr-Gly-Met-Leu-Glu-Asp-Gly-Lys-Lys-Phe-Asp, as determined by gas phase sequencing on an Applied Biosystems 477A Protein Sequencer and a Milligen/Biosearch Prosequencer 6000 Series. The "X" designation refers to an amino acid which has not been definitively identified as yet, which may be cysteine or histidine.

The HCB protein, per se or immobilized, can be used as a specific binding partner to a variety of binding ligands for diagnostic, purification or investigatory procedures. A preferred immobilizing matrix is cyanogen bromide activated Sepharose (Pharmacia) to which the HCB protein can be covalently linked, forming an affinity chromatography column.

The HCB protein is of physiological importance because of the high specificity for binding active forms of the immunosuppressant, FK-506. The above described immobilized affinity matrix can be prepared which reversibly binds FK-506 in a complex, which can be eluted with aqueous buffer reagents of increasing ionic strength The formed affinity matrix can also be used to detect FK-506-like macrolide substances by displacement of tritiated (³H)-FK-506. This would include FK-520, FK-523, FK-525 and other FK-506 analogs as disclosed in EPO Publication No. 0184162.

The matrix also provides a method to identify and/or quantify FK-506 in serum and other body fluids as well as detect FK-506 like cellular constituents which may be natural ligands.

Still further, the matrix is useful in screening candidate chemical structures that, like FK-506, can have immunosuppressive activity and, therefore, is useful in the development of other classes of drugs that function through the action of this protein.

Since the HCB protein has been purified to homogeneity, oligonucleotide probes can be used to identify the gene thereby allowing the protein to be Produced by known recombinant DNA techniques.

A typical procedure for the purification of the HCB protein is described in following Example 1.

Since, the HCB protein has an affinity for the immunosuppressant FK-506, and its active analogs, it or certain derived chemicals and/or natural derivatives thereof, including subfragments of the whole protein, can be used as a specific binding partner for these ligands in numerous receptor binding procedures known in the art.

Similarly, it can be used to purify a desired ligand from a composition containing ligand. For example, the HCB protein can be used for purifying FK-506 or related structures from a yeast fermentation broth in which the FK-506 is produced. Further, it can be used to select compounds which bind to the HCB protein as a screening test for identifying new immunosuppressant drugs. In these various procedures, it is preferred, although not required, to immobilize the HCB protein. This can be accomplished by any procedure known in the art. A particularly useful support for immobilizing proteins is cyanogen bromide treated Sepharose (CNBR-activated Sepharose 4B, Pharmacia, Piscataway, N.J.). The immobilized HCB protein is prepared by mixing the protein under basic conditions with the cyanogen bromide-activated Sepharose. The binding of the HCB protein to this matrix can result in a marked stabilization of the bound activity through a three-dimensional stabilization achieved by multiple bonds through the amino groups of the HCB protein.

The preferred immobilized HCB protein can also be used diagnostically for the determination of the concentration of FK-506 and its metabolites from physiological fluids, e.g. body fluids, and tissue extracts as for example in patients who are undergoing FK-506 immunosuppressive therapy.

The protein can also be used in an assay to bind FK-506 type macrolide compounds and biologically useful ligands, by allowing the HCB protein and FK-506 type macrolide/ligand to form a complex in an excess of the macrolide, then eluting the mixture through a column and analyzing the concentration of the pure complex Spectrophotometrically or by scintillation counting. By this methodology, pure samples of the complex can be formed, from which the macrolide or biologically useful ligand can be isolated by interrupting the binding with an e.g. strong ionic salt solution and followed by conventional chromatographic separation.

Various changes and modifications can be made in the products and processes of the present invention without departing from the spirit and scope thereof. The various embodiments which have been set forth herein and the following example are for the purpose of further illustrating the invention but are not intended to limit it.

EXAMPLE 1

Purification of the FK-506 Binding Protein

Human Jurkat cells were cultured in RPMI 1640 media containing 1% Pen/Strep, 1 mM glutamine and 10% heat-inactivated fetal calf serum. Approximately $70 \times 10^9$ cells were washed in PBS and pelleted by low speed centrifugation. The cell pellet was resuspended in 4 volumes of lysis buffer containing; 10 mM Tris-HCl, pH 7.5, 100 mM KCl, 5 mM 2-mercaptoethanol, 1 mM PMSF and 1 mM EDTA. The cells were disrupted by dounce homogenization (20 strokes) and centrifuged at $500 \times g$ for 20 min to remove nuclei and cell debris. The supernatant (S-100) was centrifuged at $100,000 \times g$ for 1 hour to remove crude membranes. The S-100 (127 ml, 8.06 mg/ml protein determined by the Bradford assay with BSA as a standard) was transferred to a glass flask and heated for 20 min, with gentle shaking, in a 56° C. water bath. Predipitated protein was removed by centrifugation and the supernatant (114 ml, 2.59 mg/ml) concentrated by filtration through an Amicon YM5 membrane and dialyzed for 8 hrs against several liters of buffer containing; 5 mM 2-mercaptoethanol, 1 mM PMSF and 1 mM EDTA. The peak of activity, which eluted at approximately 50 mM KH$_2$PO$_4$, was dialyzed against buffer containing; 20 mM NaH$_2$SO$_4$, 50 mM NaH$_2$SO$_4$, pH 6.8, 5 mM 2-mercaptoethanol, 1 mM PMSF and 1 mM EDTA and concentrated as before. The protein (2 ml, 0.64 mg/ml) was size fractionated by HPLC on a TSK-125 gel filtration column (21×600 mm, Bio-Rad). The peak of activity was pooled and dialyzed against buffer containing; 5 mM NaH$_2$PO$_4$, PH 6.8, 5 mM 2-mercaptoethanol, 1 mM PMSF and 1 mM EDTA. The protein was concentrated to 2.2 ml (0.64 mg/ml) and fractionated by weak ion exchange on a SynChropak CM 300 column (4.6×250 mm, SynChrom, Inc.). Protein was eluted isocratically with buffer of the same composition as the dialysis buffer. The peak of activity was concentrated to 0.77 ml (0.17 ng/ml) and stored at 0° C. SDS-PAGE of the CM 300 material revealed a single band (by combined silver and Coomassie blue staining) at a molecular weight of 10-11,000. Amino terminal sequence analysis of the same material revealed a single terminus.

EXAMPLE 2

Tritrated Dihydro FK-506

Purified HCB protein was mixed with tritrated dihydro FK-506, in the wells of a microtiter plate and incubated at R.T. for 5 min. The mixtures were loaded onto 2 ml minicolumns of Sephadex LH-20 (Pharmacia). The elutions were made with 0.5 ml of 30 mM phosphate buffer, pH 7.2 with 0.02% sodium azide and collected. The amount of bound tritrated dihydro FK-506 was quantitated by the use of a scintillation counter.

EXAMPLE 3

Two papers [Takahashi, et al., Nature, 337, 473 (1989) & Fischer, et al., Nature, 337, 476 (1989)] demonstrate that cyclophilin is a peptidyl-proline isomerase (PPIase). The function of this enzyme is the catalysis of cis-trans isomerization of proline residues in proteins; a step important for the folding of proteins into their native conformations. It has further been demonstrated that cyclosporin A (CsA) inhibits the PPIase activity of cyclophilin. It has been suggested that cyclophilin PPIase activity may be part of an important signal transduction pathway in lymphocytes and other cells.

In view of the similarities between cyclophilin and the HCB protein (e.g. cytosolic localization, low molecular weight, immunosuppressant binding, etc.), we assayed the pure, homogeneous HCB protein of the instant invention for PPIase activity under the same conditions used for cyclophilin. In addition, since the results were not a prior predictable, we examined the effects of CsA and FK-506 in these assays.

The assay used was essentially the same as described by K. Lang and F. Schmidt [Nature, 331, 453 (1988)]. Briefly, the PPIase assay measures the "cis" to "trans" isomerization of the proline-alanine peptide bond in the peptide, N-succinyl-Ala-Ala-Pro-Phe-p-nitroanilide. When in the "trans" form, the peptide is readily cleaved by chymotrypsin and the appearance of p-nitroanilide can be quantitated spectrophotometrically at 405 nm. The assay exhibits a high blank since 88% of the substrate is present in the "trans" form at equilibrium. In addition, the assay exhibits an appreciable nonenzymatic rate of "cis" to "trans" conversion (k=0.05 sec$^{-1}$ at 25° C. in 100 mM Tris-HCl, pH 7.8.). A summary of the assay is given in FIG. 6.

Reaction mixtures (1.0 ml) contained, 0.1 mM N-succinyl-Ala-Ala-Pro-Phe-p-nitroanilide (Bachem) (30 μl addition of 2.1 mM stock in DMSO), 100 mM Tris-HCl, pH 7.8, cyclophilin as purified by the method described by Harding et al., J. Biol. Chem., 261, p. 8547 (1986) or FK-506-binding protein and where indicated either CsA, FK-506 or dihydro FK-506. After 1.0 minutes, 30 ul of 2.0 mg/ml chymotrypsin (Sigma) in 100 mM Tris-HCl, pH 7.8 was added. After brief mixing, the absorbance was monitored at 405 nm in either a Perkin-Elmer 4B or Beckman DU 68 spectrophotometer. Absorbance measurements were taken at 3 or 5 second intervals for 4 minutes. A plot of Abs$_{405}$ [steady state]—Abs$_{405}$ [time=t] versus time was made on semi-log paper. From the straight line, the time constant for Abs$_{405}$ [steady state]—Abs$_{405}$ [time=t] to fall by 1/e was calculated. The reciprocal of this constant yields the rate constant k.

Figure 7A:
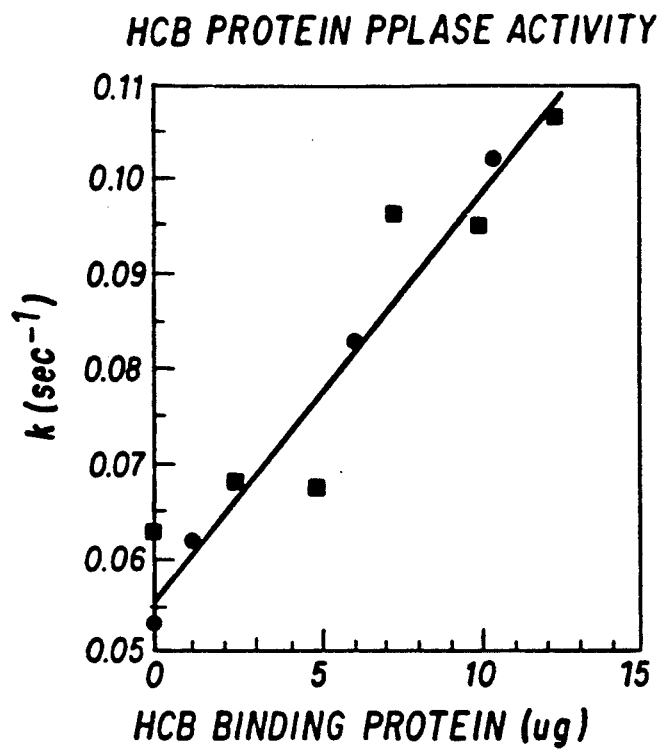
FIG. 7 illustrates in (A), the PPIase activity of the HCB protein of this invention, and (B), the PPIase activity of cyclophilin.
Figure 7B:
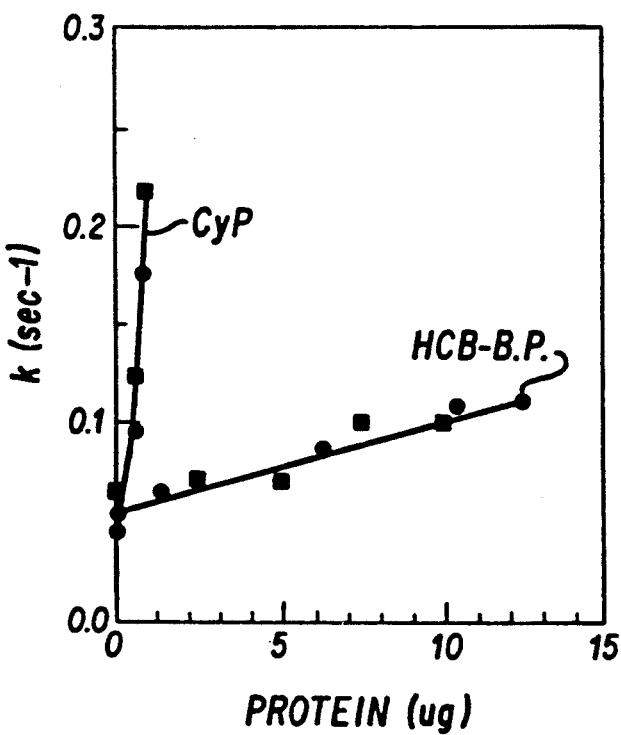

Two preparations of HCB protein isolated from different batches of JURKAT cells as described in Example 1 were assayed for PPIase activity as described above. As illustrated in FIG. 7A, the HCB protein exhibits a low, but significant PPIase activity. The increase in isomerization rate is proportional to the concentration of HCB protein. Cyclophilin PPIase activity is approximately 25 fold higher than that of the HCB protein (FIG. 7B). The reason for the differences in activity may reflect substrate specificity or reaction conditions.

Figure 8A:
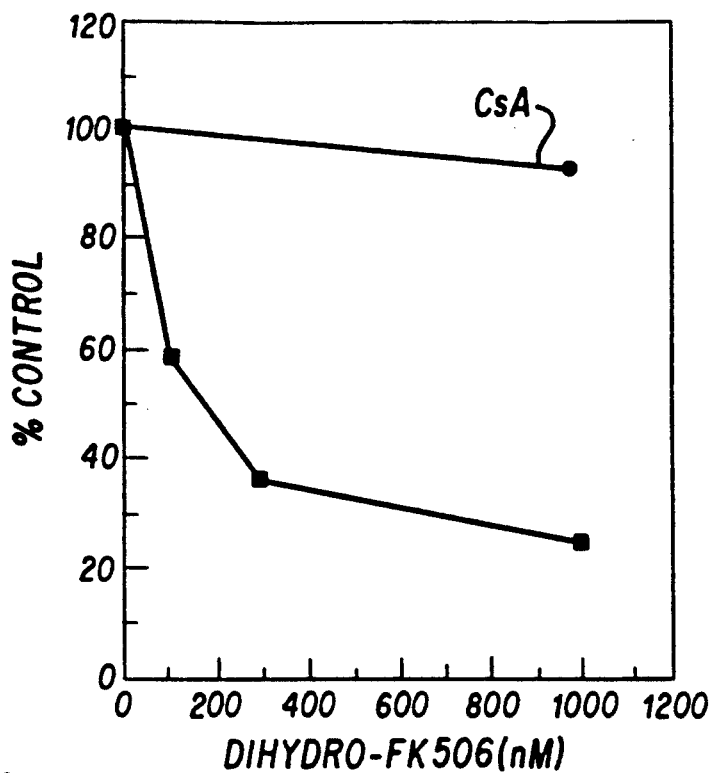
FIG. 8 illustrates in (A), the specific inhibition of HCB protein PPIase activity by dihydro-FK-506 and (B, the specific inhibition of cyclophilin PPIase activity by cyclosporine A (CsA).
Figure 8B:
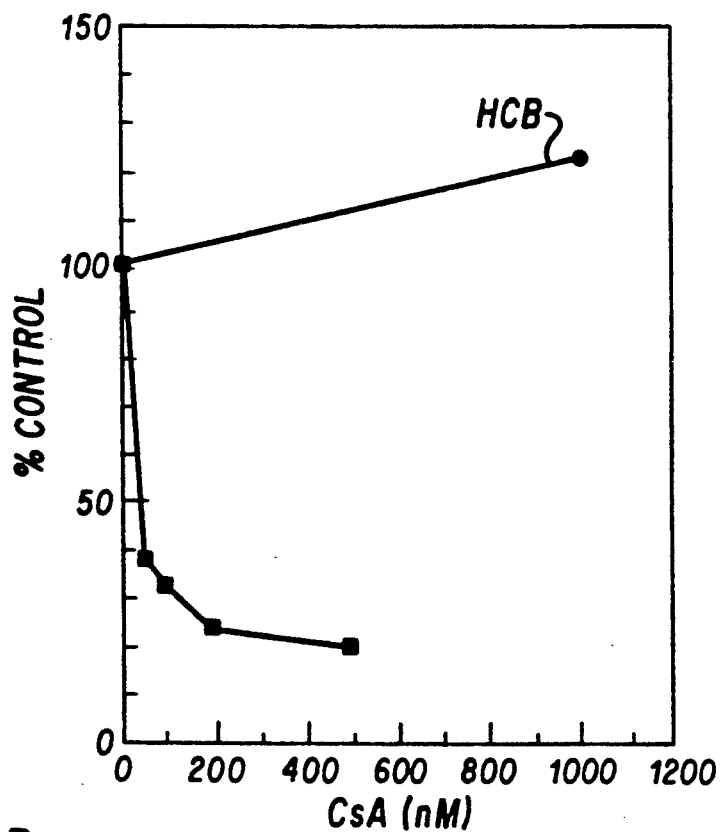

Dihydro-FK-506 specifically inhibits HCB protein PPIase activity (FIG. 8A). CsA, at a concentration of 1 uM was without effect. CsA, however, specifically inhibits cyclophilin PPIase activity (FIG. 8B). FK-506 at a concentration of 1 uM had no effect on cyclophilin PPIase activity.

The data presented demonstrates that the HCB protein, like cyclophilin, unexpectedly has been discovered to possess peptidyl-proline isomerase activity. Although the activity associated with the HCB protein is significantly less than that of cyclophilin, it is specifically inhibited by FK-506 and not CsA, suggesting that it does not represent cyclophilin contamination. The association of PPIase activity with both cyclophilin and the HCB protein implies that this activity is important during T-cell activation. Furthermore, screening assays can be devised using the assay described above, by one skilled in the art, to identify specific inhibitors which are novel immunosuppressive agents.

What is claimed is:

1. A method for detecting a biologically useful ligand comprising contacting Homogeneous Cytosolic Binding Protein ("HCB") having a specific binding affinity for FK-506 with a sample comprising a biologically useful ligand having binding affinity for said HCB under conditions, and for a time, sufficient for complex formation between said HCB and said ligand, and measuring complex formation.

2. The method of claim 1 wherein said ligand is an immunosuppressant or an antibody to the HCB protein.

3. The method of claim 1 wherein said ligand is an FK-506 type immunosuppressant.

4. The method of claim 1 wherein said ligand is FK-506, FK-520, FK-523 or FK-525.

5. The method of claim 1 wherein said ligand is FK-506.

6. The method of claim 1 wherein said HCB protein is immobilized.

7. The method of claim 1 wherein said sample comprises a fermentation broth, body fluid, or a chemical substance that is an immunosuppressant drug.

8. A method for purifying a biologically useful ligand comprising contacting Homogeneous Cytosolic Binding Protein ("HCB") having a specific binding affinity for FK-506 with a sample comprising a biologically useful ligand having binding affinity for said HCB under conditions, and for a time, sufficient for complex formation between said HCB and said ligand, isolating said complexes, interrupting the association of the components forming the complexes, and chromatographically isolating the biologically useful ligand.

* * * * *